US00PP12233P2

(12) United States Plant Patent
Lemon et al.

(10) Patent No.: US PP12,233 P2
(45) Date of Patent: Nov. 27, 2001

(54) VARIETY OF GERANIUM NAMED 'GLOBAL SANGRIA'

(75) Inventors: David G. Lemon, Lompoc, CA (US); Wendy Oglevee-O'Donovan, Scottdale, PA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/470,389

(22) Filed: Dec. 22, 1999

(51) Int. Cl.[7] ..... A01H 5/00
(52) U.S. Cl. ..... Plt./332
(58) Field of Search ..... Plt./332

*Primary Examiner*—Bruce R. Campell
*Assistant Examiner*—Annette Para
(74) *Attorney, Agent, or Firm*—Webb Ziesenheim Logsdon Orkin & Hanson, P.C.

(57) ABSTRACT

An ivy geranium plant with striking blooms streaked in variations of burgundy, purple, magenta, and white over medium green foliage.

1 Drawing Sheet

BACKGROUND OF THE INVENTION

This discovery relates to a new and distinct variety of *Pelargonium xpeltatum* identified by the varietal name of 'Global Sangria' and Oglevee, Ltd. No. 8100. The new variety was discovered in a selective breeding program at Oglevee, Ltd. in Connellsville, Pa. The new variety is a selection from the crossing of 'Global Merlot' (U.S. Plant Pat. No. 11,733) and the variety 'Peppermint Candy' (unpatented). The dark maroon bloom color of 'Global Sangria' is similar to that of 'Global Merlot' but with a white streak as on 'Peppermint Candy'. The plant habit is similar to 'Global Merlot' and not as long and vining as 'Peppermint Candy'. Cutting productions, rooting speed and post-harvest production and similar to 'Global Merlot'. The new variety was first asexually reproduced on Jan. 21, 1999 in Connellsville, Pa. and has been found to retain its distinctive characteristics through successive generations. The plant was propagated asexually by cutting.

The new variety when grown in a glass greenhouse in Connellsville, Pa. using full light, 60° F. night temperature and 68° F. day temperature and grown in soilless media with constant fertilizer at 200–250 ppm nitrogen and potassium has a response time of 6 weeks to flowering from a rooted cutted in a 10 cm pot. The time to produce a root cutting is 25 to 28 days.

DESCRIPTION OF THE DRAWING

The accompanying photographic drawing illustrates the new variety 14 weeks from rooted cutting, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee La., Connellsville, Pa. 15425. The color readings were taken under 200–220 footcandles of cool white fluorescent light on Aug. 3, 1999. Color references are to the R.H.S. Colour Chart of The Royal Horticultural Society of London and common color names.

THE PLANT

Classification:
- *Botanical.*—*Pelargonium xpeltatum.*
- *Varietal.*—Ivy geranium named 'Global Sangria'.

Form: Cascading mound.
Height: 12.5–14.0 cm from media.
Growth: Cascading growth suitable for a hanging basket.
Strength: Needs no artificial support.
Foliage: Stalked leaf attachment.
Leaves:
- *Size.*—6.0–7.0 cm across.
- *Shape.*—Reniform with cordate base.
- *Margin.*—Pedately lobed.
- *Texture.*—Leathery, pubescent.
- *Arrangement.*—Alternate, sometimes oppostie.
- *Color.*—Top: Green Group 137A. Bottom: Yellow-Green Group 144A. Zone: Small insignificant zone of Greyed-Purple Group 187A present on only some leaves.
- *Ribs and veins.*—Venation: Palmate. Color: Yellow-Green Group 144A.

Petioles:
- *Length.*—4.0–7.0 cm.
- *Color.*—Yellow-Green Group 144A.
- *Texture.*—Pubescent.

Stem:
- *Color.*—Yellow-Green Group 144B.
- *Internode length.*—2.0–3.0 cm.
- *Texture.*—Pubescent.

THE BUD

Shape: Elongated elliptical cluster.
Size:
- *Umbel.*—4.5–6.3 cm across when just showing color.
- *Bud.*—0.7–1.0 cm wide when just showing color; 1.5–2.0 cm long.

Sepals: A ring of 5 to 7 sepals is present; texture is pubescent; size is 3 to 5 mm wide and 1.4 to 1.6 cm long; color is Yellow-Green Group 144A.

INFLORESCENCE

Blooming habit: Continuous flowering. Blooming period is 11 to 14 days and the duration of the bloom is 6 to 7 days.

Borne: Umbel, florets on pedicel, pedicel on peduncle.
Open florets:
*Size of fully open bloom.*—8.0–9.0 cm across.
*Form.*—Slightly cupped.
*Color.*—Upper side of florets: Color and streaking pattern is unique to each petal; some petals are solid purple/burgundy, while others are nearly solid white with only a thin edge of color lining each petal. Most petals have an edging of the deep purple/burgundy color fading to a lighter purple color toward the center and the center is white or nearly white. Color range includes deep, dark, royal purple to a lighter magenta/purple. The petal outer edge is colored from Greyed-Purple Group 187A to Greyed-Purple Groups 187B and 187C and to Red-Purple Group 59A. Toward the center of the petal, the color fades to Red-Purple Group 71B and Red-Purple Groups 66A and 66B. Streaking of various colors is noticeable with the streaks being composed of many small dots of color including Red-Purple Groups 61B, 61C, and 74A, and Purple Group 77C. Centers of the petals are white or white with small specks of color including Purple Group 77D giving it an overall pastel appearance. Some petals have no white or light area with the lightest color on the center of these petals including Red-Purple Group 74A. Near the base of the petal, the color fades to Red-Purple Group 60A or 61B. The base of petal is white. Underside of florets: Outer edge of bottom of petal is darkest having a color range which includes Greyed-Purple Group 187A and Red-Purple Group 60A. Moving toward the center there are small dots of color which compose the streaking and spotting pattern. On some petals, there is no streaking and the petals are colored a nearly solid Red-Purple Group 61A. Other petals have much streaking and appear to be white with streaks of colors which include Red-Purple Groups 61A, 61B, and 67A. Eye: None
Petals:
*Number.*—10–15.
*Size.*—1.0–2.0 cm wide; 2.5–3.3 cm long.
Texture and appearance: Highly reflective, velvety, smooth.
Tonality from a distance: Streaked burgundy and white flower above a medium green foliage.
Petaloids:
*Quantity.*—0–3.
*Shape.*—Irregular; twisted, tubular, petal-like with cut edges.
*Color.*—Same as petals.
Pedicel:
*Length.*—2.5–3.3 cm.
*Color.*—Yellow-Green Group 144A.
*Texture.*—Pubescent.
Peduncle:
*Length.*—10.5–12.5 cm.
*Color.*—Yellow-Green Group 144A.
*Texture.*—Pubescent.
Disease resistance: Not known.
Lasting quality: Blooming is continuous with new buds replacing old buds quickly.
Flower fragrance: None.

REPRODUCTIVE ORGANS

Stamens:
*Number.*—7 to 9.
*Anthers.*—2–3 mm long.
*Filaments.*—Length: 1.0–1.4 mm. Color: White Group 155A.
*Pollen.*—Orange-Red Group 34B.
Pistils:
*Number.*—1.
*Length.*—1.3–1.5 cm.
*Stigma color.*—Greyed-Purple Group 187B.
*Style.*—3–4 mm long.
*Ovaries.*—Length: 7–8 mm. Color: Yellow-Green Group 148D.
Fruit: None observed.
Seed: Not produced.

GENERAL CHARACTERISTICS

'Global Sangria' adds a new and distinct color to the 'Global' series. This variety has the streaking agent from the parent plant 'Peppermint Candy'. The plant has a striking variety of colors and appearances ranging from a deep burgundy-velvet appearance to a white flower with deep purple or dark magenta edges and some streaking. Some tops of petals and nearly all bottoms of petals appear to have an airbrush quality with small specks of color blending to make the overall color. The variation in the streaking gives each petal a unique appearance and lends a very interesting quality to the plant.

I claim:

1. A new and distinct variety of geranium plant named 'Global Sangria' as described and illustrated herein.

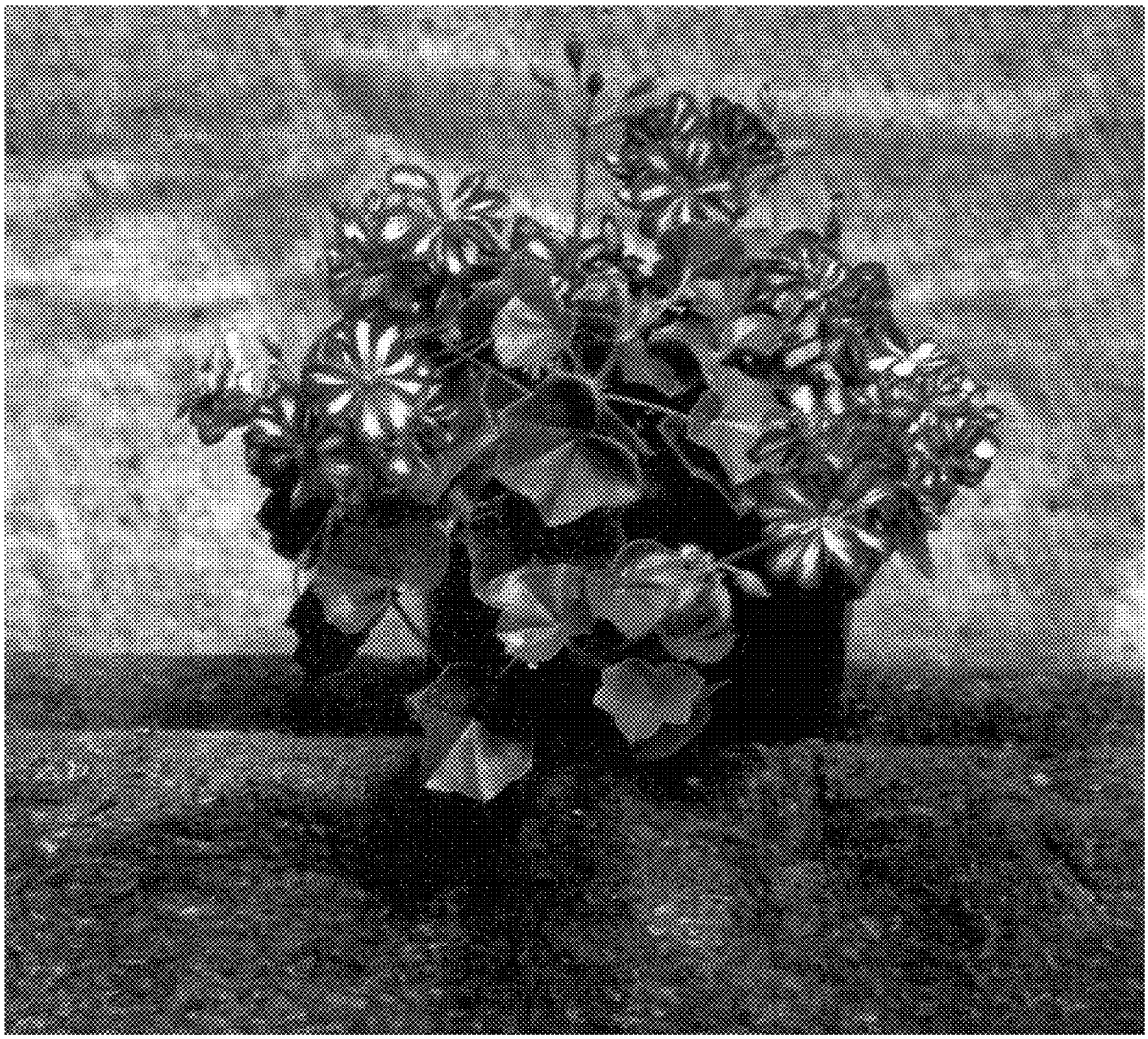

* * * * *